United States Patent [19]

Morimoto et al.

[11] Patent Number: 4,696,760

[45] Date of Patent: Sep. 29, 1987

[54] METHOD FOR PRODUCTION OF AQUEOUS DISPERSION OF N-SUBSTITUTED N',N'-ALKYLENE UREA

[75] Inventors: Yutaka Morimoto, Yokohama; Minoru Saotome, Ebina; Atsushi Komai, Yokohama, all of Japan

[73] Assignee: Nippon Shokubai Kagaku Kogyo Co., Ltd., Osaka, Japan

[21] Appl. No.: 678,247

[22] Filed: Dec. 5, 1984

[30] Foreign Application Priority Data

Dec. 8, 1983 [JP] Japan .................. 58-230613
Dec. 9, 1983 [JP] Japan .................. 58-231347

[51] Int. Cl.⁴ .................. C09K 3/00; B01J 13/00; C07D 203/12
[52] U.S. Cl. .................. 252/314; 252/8.8; 252/182; 252/311; 106/287.2; 548/966
[58] Field of Search .................. 260/239 E; 548/966; 252/8.8, 182; 106/287.2; 252/314

[56] References Cited

U.S. PATENT DOCUMENTS 2,314,968 3/1943 Bestian et al. .................. 8/191 X

FOREIGN PATENT DOCUMENTS 795380 5/1958 United Kingdom .................. 548/966
799045 7/1958 United Kingdom .
1031266 6/1966 United Kingdom .................. 260/239 E

OTHER PUBLICATIONS

F. B. Jones, et al., "The In Situ Polymerization of Ethylene Ureas and Ethylene Amides within the Fibers of Cotton", Textile Res. J., 31, 57-65 (1961).
Schwartz, et al., Surface Active Agents & Detergents, (vol. II), Interscience Pub., N.Y., (1958), pp. 671-684.

*Primary Examiner*—Donald G. Daus
*Assistant Examiner*—William A. Teoli, Jr.
*Attorney, Agent, or Firm*—Omri M. Behr

[57] ABSTRACT

A method for the production of an aqueous dispersion of a water insoluble N-substituted N',N'-alkylene urea having the general formula I:

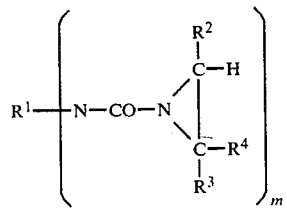

wherein $R^1$ denotes alkyl having 6 to 20 carbon atoms, phenyl or

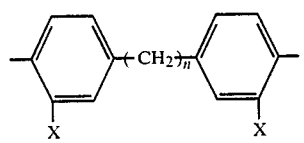

in case of m=1, or $R^1$ denotes alkylene having 6 to 20 carbon atoms, phenylene or

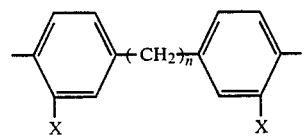

in case of m=2, where X denotes H, $CH_3$ or $OCH_3$ and n is 0 or 1, $R^2$ denotes H or $CH_3$, $R^3$ denotes H, $CH_3$ or $C_2H_5$ and $R^4$ denotes H or $CH_3$, by the reaction of an alkylene imine having 2 to 4 carbon atoms with an isocyanate represented by the general formula II:

R—NCO (II)

wherein R denotes an alkyl having 6 to 20 carbon atoms, (Abstract continued on next page.)

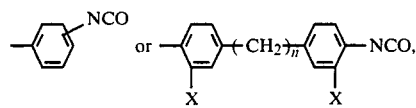
wherein X and n are the same as above in the presence of at least one surface active agent selected from the group consisting of anionic surface active agents and nonionic surface active agents under vigorous stirring.
16 Claims, 1 Drawing Figure

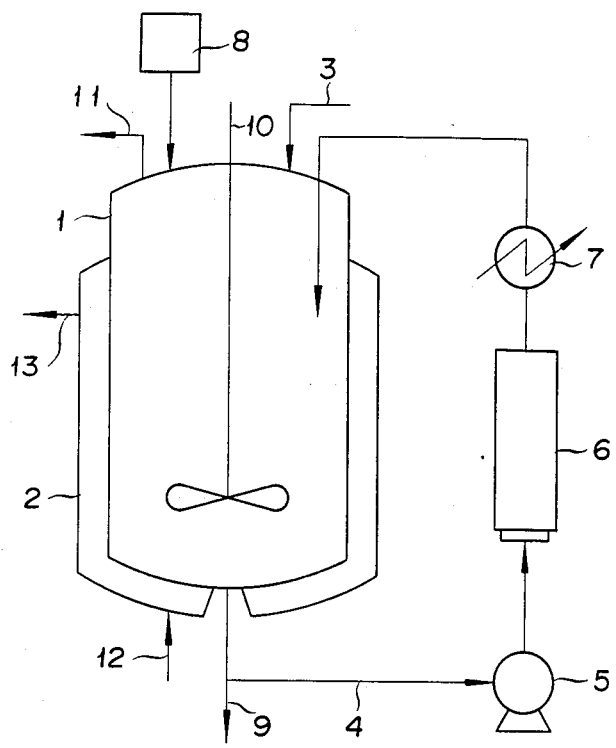

METHOD FOR PRODUCTION OF AQUEOUS DISPERSION OF N-SUBSTITUTED N',N'-ALKYLENE UREA

BACKGROUND OF THE INVENTION

1. Field of the Invention

This invention relates to a method for the production of an aqueous dispersion of a N-substituted N',N'-alkylene urea. More particularly, this invention relates to a novel method for the production of an aqueous dispersion of a N-substituted N',N'-alkylene urea by the reaction of an alkylene imine with an isocyanate.

2. Description of Prior Art

Such N-substituted N',N'-alkylene ureas as diphenylmethane-bis-4,4'-N,N'-dialkylene ureas (hereinafter referred to as "DPU") and N-alkyl-N',N'-alkylene ureas are compounds known to the art and are utilized extensively as cross-linking agent for resin, textile processing agents such as softening agent, waterproofing agent and wrinkleproofing agent, paint and ink, and resin modifiers. Further, because they have high cross-linking rates and are capable of treatments at low temperatures, they prove to be important industrial materials [Textile Res. J. 31, 57 (1961)].

Heretofore, water insoluble N-substituted N',N'-alkylene urea powders have been handled, in most cases, as dissolved in organic solvents such as dimethylformamide (DMF), dioxane, acetone and alcohols. These N-substituted N',N'-alkylene ureas, when handled in the form of dust and suffered to be inhaled, can cause harm to the human body and, when handled in the form of a solution in an organic solvent without due care, can induce fire hazard. In the circumstance, the desirability of handling these compounds in a safer and more convenient form of aqueous dispersion instead of powder or solution has found growing recognition.

A method for producing an alkylene urea by causing an alkylene isocyanate having at least 10 carbon atoms to react with ethylene imine in water preferably in the presence of a dispersant or an emulsifier has been known to the art (British Pat. No. 799,045). By such methods, stable aqueous dispersion cannot be obtained, unless the other component is added into the resulted aqueous dispersion.

An object of this invention, therefore, is to provide a novel method for the production of an aqueous dispersion of a N',N'-alkylene urea.

Another object of this invention is to provide a novel method for the production of a stable aqueous dispersion of a N-substituted N',N'-alkylene urea by the reaction of an alkylene imine with an isocyanate in water in the presence of a specified surface active agent.

SUMMARY OF THE INVENTION

The objects described above are accomplished by a method for the production of an aqueous dispersion of a water insoluble N-substituted N',N'-alkylene urea having the general formula I:

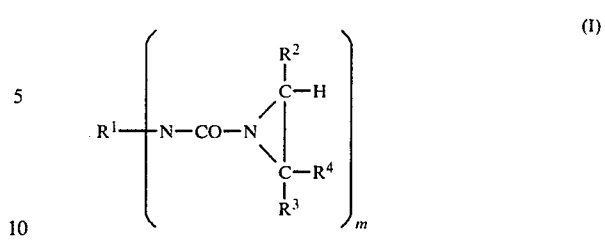

wherein $R^1$ denotes alkyl having 6 to 20 carbon atoms, phenyl or

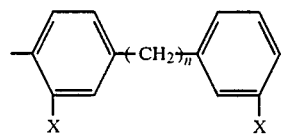

in case of m=1, or $R^1$ denotes alkylene having 6 to 20 carbon atoms, phenylene or

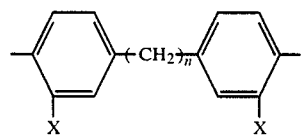

in case of m=2, where X denotes H, $CH_3$ or $OCH_3$ and n is 0 or 1, $R^2$ denotes H or $CH_3$, $R^3$ denotes H, $CH_3$ or $C_2H_5$ and $R^4$ denotes H or $CH_3$, by the reaction of an alkylene imine having 2 to 4 carbon atoms with an isocyanate represented by the formula II:

R—NCO (II)

wherein R denotes an alkyl having 6 to 20 carbon atoms,

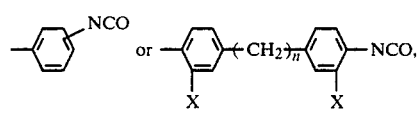

wherein X and n are the same as above in the presence of at least one surface active agent selected from the group consisting of anionic surface active agents and nonionic surface active agents under vigorous stirring.

BRIEF DESCRIPTION OF THE DRAWING

FIGURE is an example of a device for conducting a process for this invention.

DESCRIPTION OF PREFERRED EMBODIMENTS

In accordance with the present invention, a stable aqueous dispersion of a N-substituted N',N'-alkylene urea represented by the general formula I is obtained by adding an isocyarate represented by the general formula II into an aqueous solution of an alkylene imine having 2 to 4 carbon atoms in the presence of at least one surface active agent selected from the group consisting of anionic surface active agents and nonionic surface active agents and dispersing the powdered N-substituted N',N'-alkylene urea.

Alkylene imines having 2 to 4 carbon atoms are represented by the following general formula III:

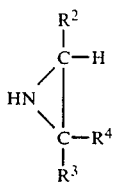

wherein $R^2$, $R^3$ and $R^4$ is the same as above. Typical alkylene imines are ethylene imine, propylene imine, 1,2-butylene imine, 2,3-butylene imine and isobutylene imine. Among other alkylene imines, ehtylene imine proves particularly desirable.

Concrete examples of the isocyanate represented by the general formula II are alkyl monoisocyanates having 6 to 20 carbon atoms, preferably 16 to 20 carbon atoms, in their alkyl groups, such as hexyl isocyanate, heptyl isocyanate, octyl isocyanate, decyl isocyanate, dodecyl isocyanate, undecyl isocyanate, hexadecyl isocyanate, heptadecyl isocyanate, octadecyl isocyanate, nonadecyl isocyanate, and eicocyl isocyanate, and aromatic diisocyanates such as 2,4-tolylene diisocyanate, 2,6-tolylene diisocyanate, 3,3'-bitolylene-4,4'-diisocyanate, dianisidine diisocyanate, diphenylmethane-4,4'-diisocyanate (MDI), and 3,3'-dimethyldiphenylmethane-4,4'-diisocyanate. Among other isocyanates, MDI proves particularly desirable.

Examples of the anionic surface active agents which are advantageously used in this invention include those of straight-chain alkylbenzene sodium sulfonate type

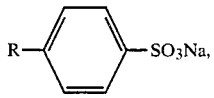

alcohol-sulfate type $R-OSO_3Na$, polyoxy-ethylenealkyl ether sulfate type $R-O(CH_2CH_2O)_nSO_3Na$, polyoxy-ethylene-alkylphenyl ether sulfate type

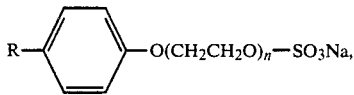

$\alpha$-olefin sulfonate type $RCH=CH(CH_2)_nSO_3Na$, dialkyl sulfosuccinate type

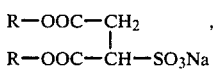

polyoxyethylene carboxylic ester sulfate type $R-COO(CH_2CH_2O)_nSO_3Na$, polyoxyethylene carboxylic ester phosphate type

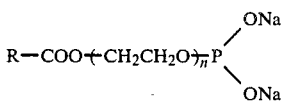

and $\beta$-naphthalene sulfonic acid-formaldehyde polycondensate type

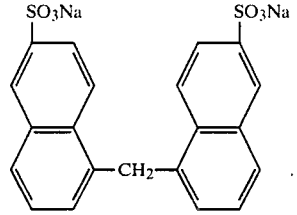

Examples of the nonionic surface active agents which are advantageously used herein include those of polyoxy-ethylene alkyl ether type $R-O(CH_2CH_2O)_nH$, polyoxyethtlene alkylaryl ether type

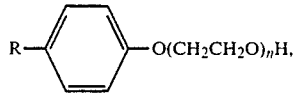

polyoxyethylene alkyl amine type

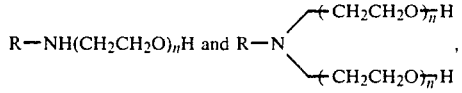

polyoxyethylene alkyl amide type

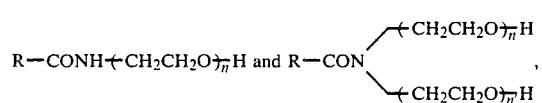

polyoxyethylene sorbitan fatty ester type

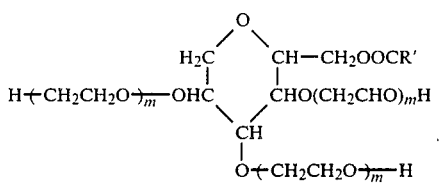

(wherein, R' represents an alkyl having 6 to 25 carbon atoms and m an integer having the value of 5 to 50), Pluronic type $HO-(CH_2CH_2O)_a(CH_3CHCH_2O)_b(CH_2CH_2O)_cH$ (wherein, a, b and c each have a value greater that 1 and the sum of a, b and c has a value of 20 to 300), the Tetronic type

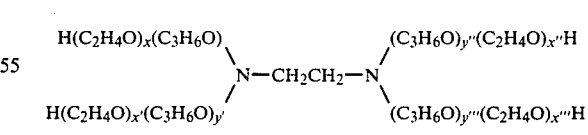

wherein, X through X''' each have a value greater than 1, y through y''' each have a value greater than 1 and the sum of X, X', X'', X''', Y, Y', Y'' and Y''' has a value of 20 to 600.

These anionic and nonionic surface active agents can be used either singly or in the form of a varying combination of anion-anion, nonion-nonion, or anion-nonion agents. Although the selection of an anionic and/or nonionic surface active agent is not particularly liminted, it is desired to be such that the HLB value of the selected surface active agent has a value of not less than 9. Particularly when an alkylene monoisocyanate is adopted, the value of HLB is desired to fall in the range of 9 to 20, preferably 10 to 16. When an aromatic diisocyanate is adopted, the value of HLB is desired to be not less than 15, preferably to be in the range of 16 to 20.

The amount of the anionic and/or nonionic surface active agent to be incorporated is in the range of 0.1 to 20% by weight, preferably 1 to 10% by weight, based on the amount of N-substituted N',N'-alkylene urea to be produced. Particularly when a nonionic surface active agent is used in the reaction using an aromatic diisocyanate, the amount of the surface active agent is in the range of 1 to 10% by weight. The aqueous dispersion of a N-substituted N',N'-alkylene urea which is obtained by the present invention is amply stable. When an anionic and/or nonionic surface active agent is further added at a proper time to the aqueous dispersion obtained as described, there can be obtained a stable aqueous dispersion.

This invention does not specifically define the reaction time between the alkylene imine and the isocyanate. The reaction temperature is required not to exceed 25° C. and desired to fall in the range of 5° to 15° C. If the reaction temperature exceeds 25° C., the reaction of isocyanate with water gives birth to a large amount of urea compounds and the reaction of alkylene imine with isocyanate is consequently impeded. Dispersion of the N-substituted N',N'-alkylene urea formed during the reaction should be conducted simultaneously with the reaction. If necessary, the isocyanate may be pulverized by a sand mill, a ball mill or the like during the reaction. During the reaction of alkylene imine with isocyanate, the mixture of the reactants should be stirred vigorously. Further, the reaction product may be stirred vigrously after completion of the reaction. This stirring is desired to be carried out with a powerful mixer such as a homo-mixer, a line mixer or a line mill. In these mixer, the liquid to be treated is inhaled from an inhalation port by utilizing pressure difference between the inhalation port and an exhalation port occured by high speed rotation of turbine and is pulverized, mixed, stirred, emulsified and dispersed by the action of shearing force, pulverization, impact, turbulence, etc. occured at fine and uniform gap between the turbine and a radial obstruction portion of a stater.

The amount of the alkylene imine relative to that of the isocyanate is in the range of 1.0 to 1.05 equivalents, preferably 1.01 to 1.03 equivalents per equivalent of the isocyanate group of the isocyanate compounds. The alkylene imine is used in an amount of 1 to 30% by weight, preferably 2 to 20% by weight, based on the amount of water as medium. In the aqueous dispersion consequently obtained, the concentration of the N-substituted N',N'-alkylene urea is in the range of 5 to 50% by weight, preferably 10 to 40% by weight.

In accordance with the present invention, there can be very easily obtained an aqueous dispersion of a N-substituted N',N'-alkylene urea having no residue of highly toxic, alkylene imine. This aqueous dispersion is safe and easy to handle because it irritates the skin and the mucous membrane only sparingly. The aqueous dispersion enjoys lasting stability and retains water-dispersibility for a very long time.

The aqueous dispersion of a N-substituted N',N'alkylene urea suits utility as textile processing agents such as sfotening agent, waterproofing agent and wrinkleproofing agent, peeling agent, mold release agent, crosslinker for resin, adhesive agent, paint, ink and resin modifier.

Now, the present invention will be described more specifically below with reference to working examples. It should be noted that this invention is not limited to these working examples.

In the examples, the produced aqueous dispersions of N-substituted N',N'-alkylene ureas were tested for stability by the following methods, Method 1 and Method 2. Method 1 for testing aqueous dispersion for stability:

A 10-g sample of a given dispersion is placed in a test tube and treated on a centrifugal separator (produced by Hitachi, Ltd. and marketed under designation of 05PR-2 type) at 4000 r.p.m. for 15 minutes. Then, a 5-g portion of the separated liquid is gently removed from the liquid surface and analyzed for N-substituted N',N'-alkylene urea concentration.

Stability (%)=[(N-substituted N',N'-alkylene urea concentration before centrifugal separation)/(N-substituted N',N'-alkylene urea concentration after centrifugal separation)]×100

By this method, the degree of stability of the aqueous dispersion increases with the increasing value (%) so reported. Method 2 for testing aqueous dispersion for stability:

A 100 g sample of a given aqueous dispersion is placed in a 100-ml measuring cylinder, left standing at rest therein at room temperature for one month, and visually examined with respect to condition of dispersion.

EXAMPLE 1

In a 500-ml tall beaker provided with a thermometer, 252.9 g of water, 0.3 g of sodium hydroxide and 3.2 g (5% by weight based on N-octadecyl-N',N'-ethylene urea) of polyoxyethylene alkyl ether (produced by Kao Atlas Co. and marketed under trademark designation of Emulgen 106, HLB=10.5) were thoroughly mixed. The resultant mixture and 8.0 g (0.186 mol) of ethylene imine added thereto were stirred in a homo-mixer at 10° C. to form a uniform solution.

Then, 56.1 g (0.190 mol) of molten octadecyl isocyanate was added dropwise into the solution through a dropping funnel. The reactants were left reacting at the same temperature for 8 hours to afford a stable aqueous dispersion having a N-octadecyl-N',N'-ethylene urea concentration of 18.4% by weight at room temperature. This aqueous dispersion was found by analysis to contain no unaltered ethylene imine.

By Method 1 the stability was found to be 75%. By Method 2, the aqueous dispersion was found to be a stably dispersed condition (substantially) free from supernatant and precipitate.

EXAMPLE 2

In the same apparatus as used in Example 1, 251.0 g of water, 0.3 g of sodium hydroxide, 5.1 g (1.2% by weight based on N-octadecyl-N',N'-ethylene urea) of polyoxyethylene alkylfulfate (produced by kao Atlas Co. and marketed under trademark designation of Emal 200, aqueous 25% by weight solution) and 8.0 g of ethylene imine were stirred in a homo-mixer at 10° C. to produce a uniform solution.

Then, 56.1 g of molten octadecyl isocyanate was added dropwise into the solution and the reactants were left reacting at the same temperature for 13 hours to produce an aqueous dispersion having a N-octadecyl-N',N'-ethylene urea concentration of 18.0% by weight at room temperature. This aqueous dispersion was found by test to contain no unaltered ethylene imine. By Method 1, the stability was found to be 80%. By Method 2, the aqueous dispersion was found to be as stable as that of Example 1.

EXAMPLE 3

In the same apparatus as used in Example 1, 249.7 g of water, 0.3 g of sodium hydroxide, 5.1 g of polyoxyethylene alkyl ether, a nonionic surface active agent, (produced by Kao-Atlas Co. and marketed under trademark designation of Emulgen 106, HLB=10.5), 1.3 g of alkyl sulfate, an anionic surface active agent (produced by Kao-Atlas Co. and marketed under trademark designation of Emal 0), and 8.0 g of ethylene imine were stirred in a homo-mixer at 10° C. to produce a uniform solution.

Then, 56.1 g of molten octadecyl isocyanate was added dropwise to the solution and the reactants were left reacting at room temperature for 24 hours to produce an aqueous dispersion. This aqueous solution was found to have a N-octadecyl-N',N'-ethylene urea concentration of 18.5% by weight. It was found by test to contain no unaltered ethylene imine.

By Method 1, the stability was found to be 82%. By Method 2, the aqueous dispersion was found to be as stable as that of Example 1.

EXAMPLE 4

In a 500-ml tall beaker provided with a thermometer, 229.6 g of water, 0.3 g of sodium hydroxide and 2.9 g (5% by weight based on N-hyxadecyl-N'N'-ethylene urea) of polyoxyethylene alkyl ether (produced by Kao-Atlas Co. and marketed under trademark designation of Emulgen 120, HLB=15.3) were thoroughly dissolved. The resultant solution and 8.0 g of ethylene imine added thereto were stirred in a homo-mixer at 10° C. to produce a uniform solution.

Then, 50.2 g of molten hexadecyl isocyanate was added dropwise into the solution through a dropping funnel and the reactants were left reacting at the same temperature for 8 hours to afford an aqueous dispersion having a N-hexadecyl-N',N'-ethylene urea concentration of 18.0% by weight at room temperature. This aqueous dispersion was found by test to contain no unaltered ethylene imine. By Method 1, the stability was found to be 70%. By Method 2, the aqueous dispersion was found to be as stable as that of Example 1.

Control 1

In the same apparatus as used in Example 1, 252.9 g of water, 0.3 g of sodium hydroxide and 8.0 g of ethylene imine were stirred in a homo-mixer at 10° C. to afford a uniform solution.

Then, 56.1 g of molten octadecyl isocyanate was added dropwise into the solution through a dropping funnel. The reactants were left reacting at the same temperature. During the course of this reaction, the reaction mixture gelled and the reaction could not be continued any further. Thus, no aqueous dispersion of N-octadecyl-N',N'-ethylene urea was obtained.

EXAMPLE 5

In a 500-ml tall beaker provided with a thermometer, 243.1 g of water, 0.3 g of sodium hydroxide and 4.1 g (5% by weight based on diphenylmethane-bis-4,4'-N'N'-diethylene urea) of polyoxyethylene nonylphenol ether (produced by Kao-Atlas Co. and marketed under trademark designation of Emulgen 985, HLB=18.9) were thoroughly dissolved. The resultant solution and 20.7 g of ethylene imine added thereto were stirred in homo-mixer at 10° C. to afford a uniform solution.

Then, 61.8 g of molten MDI was added dropwise into the solution through a dropping funnel and the reactants were left reacting at a temperature of 10° C. for 8 hours to produce a stable aqueous dispersion having a diphyenylmethane-bis-4,4'-N,N'-diethylene urea concentration of 23.8% by weight. This aqueous dispersion was found by test to contain no unaltered ethylene imine.

By Method 1, the stability was found to be 78%. By Method 2, the aqueous dispersion was found to be in a stable dispersed condition (substantially) free from supernatant and precipitate.

EXAMPLE 6

In the same apparatus as used in Example 5, 242.4 g of water, 0.3 g of sodium hydroxide, 4.8 g (1.5% by weight based on diphenyl methane-bis-4,4'-N,N'-diethylene urea) of sepcial carboxylic acid type high-molecular active agent (an aqueous 25% by weight anionic surface active agent solution produced by Kao-Atlas Co. and marketed under trademark designation of Demol EP) and 20.7 g of ethylene imine were stirred in a homo-mixer at 10° C. to produce a uniform solution.

Then, 61.8 g of molten MDI was added dropwise to the solution and the reactants were left reacting at the same temperature for 12 hours, to produce an aqueous dispersion having a diphenyl-methane-bis-4,4'-N,N'-diethylene urea concentration of 23.5% by weight. This aqueous dispersion was found by test to contain no unaltered ethylene imine.

By Method 1, the stability was found to be 80%. By method 2, this aqueous dispersion was found to be as stable as that of Example 1.

EXAMPLE 7

In the same apparatus as used in Example 5, 235.0 g of water, 0.3 g of sodium hydroxide, 7.4 g of polyoxyethylene nonylphenol ether, a nonionic surface active agent (produced by Kao-Atlas Co. and marketed under trademark designation of Emulgen 935, HLB=17.5), 0.8 g of naphthalene sulfonic acid formaline condensate (produced by Kao-Atlas Co. and marketed under trademark designation of Demol N) and 20.7 g of ethylene imine were stirred in a homo-mixer at 10° C. to produce a homogeneous solution.

Then, 61.8 g of molten MDI was added dropwise to the solution and the reactants were left reacting for 19 hours to produce an aqueous dispersion at room temperature. It was found to have a diphenyl-methane-bis-4,4'-N,N'-diethylene urea concentration of 23.2% by weight. This aqueous dispersion was found by test to contain no unaltered ethylene imine.

By Method 1, the stability was found to be 85%. By method 2, the aqueous dispersion was as stable as that of Example 1.

Control 2

In the same apparatus as used in Example 5, 243.1 g of water, 0.3 g of sodium hydroxide and 20.7 g of ethylene imine were stirred in a homo-mixer at 10° C. to produce a uniform solution.

Then, 61.8 g of molten MDI was added dropwise into the solution through a dropping funnel. The reactants were left reacting at the same temeperature. During the course of the reaction, the reaction mixture gelled and the reaction could not be continued any further. Thus, no aqueous dispersion of diphenyl-methane-bis-4,4'-N,N'-diethylene urea could be obtained.

EXAMPLE 8

In a 100 liter of a stirring vessel 1 as shown in a drawing provided with a thermometer (not shown), a stirrer 10, an isocyanate dropping vessel 8, a feeding pipe 3, a vent pipe 11, a discharging pipe 9 and a jacket 2, 63.2 kg of water, 75 g of sodium hydroxide and 0.8 kg (5% by weight based on N-octadecyl-N',N'-ethylene urea) of polyoxyethylene alkyl ether (produced by Kao-Atlas Co. and marketed under trademark designation of Emulgen 106, HLB=10.5) were charged by the feeding pipe 3 and thoroughly solubilized. 2.0 kg of ethylene imine was added into the resultant mixture and was stirred at 10° C. to form a uniform solution.

Then, the solution was recycled to an outer recycling pipe 4 provided with a pump 5, a line mill (manufactured by Tokushu Kika Co.) 6 and a heat exchanger 7 by the pump 5, and at the same time 14.0 kg of molten octadecyl isocyanate was added dropwise into the solution through the dropping vessel 8. The temperature of the reactants in the stirring vessel were maintained at 10° to 15° C. by charging a 50% by weight of aqueous ethylene glycol solution cooling medium from the pipe 12 to the jacket 2 of the stirring vessel 1 and then discharged from the pipe 13, and octadecyl isocyanate and N-octadecyl-N',N'-ethylene urea formed during the reaction in the reactants were pulverized and mixed thoroughly and reacted for 8 hours to afford a stable aqueous dispersion having a N-octadecyl-N',N'-ethylene urea concentration of 18.4% by weight at room temperature. This aqueous dispersion was found by analysis to contain no unaltered ethylene imine.

By Method 1 the stability was found to be 81%. By Method 2, the aqueous dispersion was found to be a stably dispersed condition (substantially) free from supernatant and precipitate.

EXAMPLE 9

In a stirring vessel similar to one as Example 8, 60.8 kg of water, 94 g of sodium hydroxide and 1.2 kg (5% by weight based on diphenyl methane-4,4'-N,N'-diethylene urea) of polyoxyethylene alkyl ether (produced by Kao-Atlas Co. and marketed under trademark disignation of Emulgen 985, HLB=18.9) were charged by the feeding pipe 3 and throughly solubilized 6.0 kg of ethylene imine was added into the resultant mixture and was stirred at 10° C. to form a uniform solution.

The solution was recycled to an outer recycling pipe 4 provided with a pump 5, a homo-mixer (TK Pipe Line HOMOMIXER 2S5 Type, manufactured by Tokushu Kika Co.) 6 and a heat excharger 7 by the pump 5, and at the same time 17.8 kg of molten MDI was added dropwise into the solution through the dropping vessel 8. The temperature of the reactants in the stirring vessel were maintained at 10° to 15° C. by charging a 50% by weight of aqueous ethylene glycol solution cooling medium to the jacket 2, and MDI and diphenyl methane-4,4'-N,N'-diethylene urea formed during the reaction in the reactants were pulverized and mixed thoroughly and reacted for 9 hours to afford a stable aqueous dispersion of diphenyl methane-4,4'-N,N'-diethylene urea of 25.7% by weight at room temperature. This aqueous dispersion was found by analysis to certain no unaltered ethylene imine.

By method 1 the stability was found to be 81%. By Method 2, the aqueous dispersion was found to be a stably dispersed condition (substantially) free from supernatant and precipitate.

EXAMPLE 10

Example 8 was repeated, except that a sand mill (ATTRITOR, manufactured by Mitsui Miike Seisakusho Co.) was used instead of the line mill to obtain an aqueous dispersion of N-octadecyl-N',N'-ethylene urea. This aqueous dispersion was found by analysis to contain no unattered ethylene imine. By Method 1 the stability was found to be 82%. By Method 2, the aqueous dispersion was found to be a stably dispersed condition (substantially) free from supernatant and precipitate.

EXAMPLE 11

Example 9 was repeated, except that a sand mill (ATRRITOR, manufactured by Mitsui Miike Seisakusho Co.) was used instead of the homo mixer to obtain an aqueous dispersion of diphenyl methane-4,4'-N,N'-diethylene urea. This aqueous dispersion was found by analysis to contain no unaltered ethylene imine. By method 1 the stability was found to be 82%. By Method 2, the aqueous dispersion was found to be a stably dispersed condition (substantially) free from supernatant and precipitate.

What is claimed is:

1. A method for the production of an aqueous dispersion of a water insoluble N-substituted N',N'-alkylene urea having the general formula I:

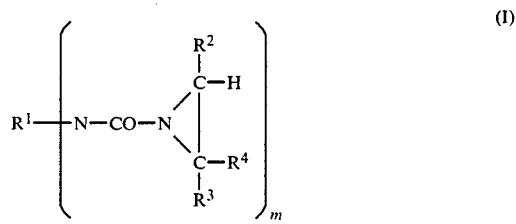

wherein $R^1$ denotes alkyl having 6 to 20 carbon atoms, phenyl or

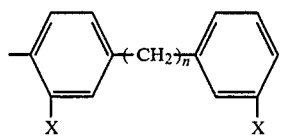

in case of m=1, or $R^1$ denotes alkylene having 6 to 20 carbon atoms, phenylene or

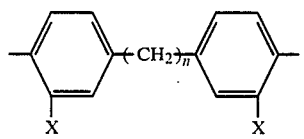

in case of m=2, where X denotes H, $CH_3$ or $OCH_3$ and n is 0 or 1, $R^2$ denotes H or $CH_3$, $R^3$ denotes H, $CH_3$ or $C_2H_5$ and $R^4$ denotes H or $CH_3$, by the reaction of an alkylene imine having 2 to 4 carbon atoms with an isocyanate represented by the general formula II:

R—NCO         (II)

wherein R denotes an alkyl having 6 to 20 carbon atoms,

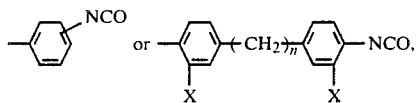

wherein X and n are the same as above in the presence of at least one surface active agent selected from the group consisting of (a) at least one anionic surface active agent selected from the group consisting of alkyl-sulfate type R—OSO$_3$Na, polyoxyethylene-alkyl ether sulfate type R—O(CH$_2$CH$_2$O)$_n$SO$_3$Na, polyoxyethylene-alkylphenyl ether sulfate type

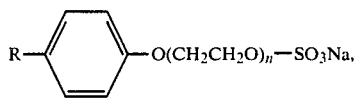

β-naphthalene sulfonic acid-formaldehyde polycondensate type

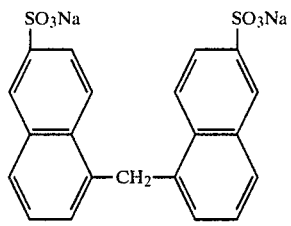

and (b) at least one nonionic surface active agent selected from the group consisting polyoxyethylene alkyl ether type R—O(CH$_2$CH$_2$O)$_n$H, polyoxyethylene alkylaryl ether type

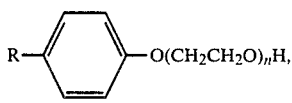

olyoxyethylene carboxylic ester type R—COO(CH$_2$CH$_2$O)$_n$H and polyoxyethylene sorbitan fatty ester type

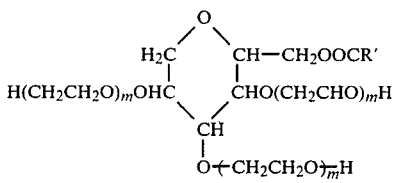

(wherein R' represents an alkyl having 6 to 25 carbon atoms and m an integer having the value of 5 to 50) at a temperature of not more than 25° C. under vigorous stirring or grinding.

2. A method according to claim 1, wherein said surface active agent is used in an amount of 0.1 to 20% by weight based on said N-substituted N',N'-alkylene urea to be produced.

3. A mthod according to claim 1, wherein the reaction temperature is in the range of 5° to 15° C.

4. A method according to claim 1, wherein said surface active agent has HLB of not less than 9.

5. A method according to claim 1, wherein the amount of said alkylene imine is in the range of 1.0 to 1.05 equivalents per equivalent of the isocyanate group of the isocyanate compound.

6. A method according to claim 1, wherein said alkylene imine is used in an amount of 1 to 30% by weight based on the amount of aqueous medium.

7. A method according to claim 2, wherein said isocyanate is an alkyl isocyanate.

8. A method according to claim 7, wherein said surface active agent has HLB in the range of 9 to 20.

9. A method according to claim 8, wherein said surface active agent is used in an amount of 0.1 to 20% by weight based on the amount of said N-substituted N',N'-alkylene urea to be produced.

10. A method according to claim 7, wherein the alkyl group of said alkyl isocyanate has 16 to 20 carbon atoms.

11. A method according to claim 2, wherein the substituent R in said general formula I is an aromatic diisocyanate represented by

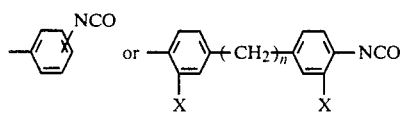

(wherein X and n have the same meanings as described above).

12. A method according to claim 11, wherein the surface active agent has HLB of not less than 15.

13. A method according to claim 11, wherein the surface active agent has HLB in the range of 16 to 20.

14. A method according to claim 12, wherein said surface active agent is used in an amount of 1 to 10% by weight based on the amount of said N-substituted N',N'-alkylene urea to be produced.

15. A method according to claim 12, wherein the aromatic diisocyanate is diphenyl-methane-4,4'-diisocyanate.

16. A method according to claim 1, wherein the stirring is carried out by a homo-mixer, a line mixer or a line mill.

* * * * *